(12) United States Patent
Hartrumpf et al.

(10) Patent No.: US 8,422,003 B2
(45) Date of Patent: Apr. 16, 2013

(54) DEVICE AND METHOD FOR THE CLASSIFICATION OF TRANSPARENT COMPONENT IN A MATERIAL FLOW

(75) Inventors: Matthias Hartrumpf, Karlsruhe (DE); Rudiger Heintz, Neupotz (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 243 days.

(21) Appl. No.: 12/681,921

(22) PCT Filed: Oct. 9, 2008

(86) PCT No.: PCT/DE2008/001662
§ 371 (c)(1),
(2), (4) Date: Apr. 7, 2010

(87) PCT Pub. No.: WO2009/049594
PCT Pub. Date: Apr. 23, 2009

(65) Prior Publication Data
US 2010/0230327 A1 Sep. 16, 2010

(30) Foreign Application Priority Data
Oct. 16, 2007 (DE) .................... 20 2007 014 466 U

(51) Int. Cl.
*G01N 21/00* (2006.01)
(52) U.S. Cl.
USPC ............................................ 356/72; 356/445
(58) Field of Classification Search .............. 356/72–73, 356/445–446, 364, 402
See application file for complete search history.

(56) References Cited

U.S. PATENT DOCUMENTS

| 3,455,637 | A | * | 7/1969 | Howard | 356/434 |
| 4,919,534 | A |   | 4/1990 | Reed | |
| 4,973,561 | A | * | 11/1990 | Hansen et al. | 356/436 |
| 5,442,446 | A |   | 8/1995 | Gerber et al. | |
| 6,060,677 | A | * | 5/2000 | Ulrichsen et al. | 209/577 |
| 6,760,103 | B2 | * | 7/2004 | Shakespeare et al. | 356/300 |
| 2003/0081206 | A1 | * | 5/2003 | Doyle | 356/301 |
| 2005/0046850 | A1 |   | 3/2005 | Chow | |
| 2006/0016735 | A1 |   | 1/2006 | Ito et al. | |
| 2006/0181708 | A1 | * | 8/2006 | Takahashi et al. | 356/432 |

FOREIGN PATENT DOCUMENTS

| EP | 0 146 299 | 6/1985 |
| EP | 0 379 281 A2 | 7/1990 |
| EP | 0 372 241 B1 | 9/1993 |

\* cited by examiner

*Primary Examiner* — Kara E Geisel
(74) *Attorney, Agent, or Firm* — Antonelli, Terry, Stout & Kraus, LLP.

(57) ABSTRACT

A device is disclosed for the classification of a transparent component of a material flow using an optical detector unit, with allocatable optical axis which is directed toward the material flow, at least one illumination unit for illuminating the material flow from a space over the material flow, in which the optical detector unit is also contained, and a classifier, which classifies the component based on information which is recorded from the component using the optical detector unit, and a decision criterion. A retroreflector is provided at least longitudinally relative to the optical axis of the detector unit, downstream from the material flow in the viewing direction of the detector, the illumination unit provides at least two light sources, with first light source emitting light of a first type and a second light source emitting light of a second type.

31 Claims, 1 Drawing Sheet

DEVICE AND METHOD FOR THE CLASSIFICATION OF TRANSPARENT COMPONENT IN A MATERIAL FLOW

BACKGROUND OF THE INVENTION

1. Field of the Invention

The invention relates to a device and a method for the classification of transparent components of a material flow. The device comprises an optical detector unit, the allocatable optical axis of which is directed toward the material flow, and at least two units for illuminating the material flow. The at least two illumination units and the detector unit are located on the same side relative to the material flow, that is, in the same half-space spanning over the material flow. The information which the detector unit receives from the components of the material flow is analyzed in a unit which has a classifier. Based on the result of the classification, control signals are generated for a unit for sorting, for example, via actuators, such as blowout nozzles or sorting shunts, or marking or logging. The material flow can be provided in the form of bulk individual objects, for example, in the form of bulk goods, or as a continuously produced coherent material, for example, flat glass or extruded partially-transparent material.

2. Description of the Prior Art

In facilities known for the automatic optical sorting of bulk goods, the material to be sorted, as much as possible in a single-ply layer, is applied on a conveyor belt, conducted through a fall shaft, or shaken over a slide. If a conveyor belt is used, it runs at a velocity of 3 m/s, for example. At the end of the conveyor belt, the material is thrown off of the conveyor belt and flies further in a trajectory. Shortly after the drop edge, an image processing system inspects the material flow. The images recorded by the camera are analyzed by a computer. The components of the bulk good flow, which is to be sorted out, are recognized on the basis of their color and optionally also their shape and blow out of the free flying material flow correctly with the aid of short blasts of compressed air.

In other forms of implementation of optical sorters, the free-flying material flow is not generated via a conveyor belt, but rather the bulk good flow slips over a slide or the bulk good flow is poured properly in the form of a freefalling material flow. For example, reference is made for this purpose to EP 0 146 299 B1, in which a channel sorter is described, in which, for example, a bulk goods flow comprising coffee beans falls through a measuring cell, in which, on one side, an illuminated background is provided and, on the other side, a detector is provided constructed by discrete photo sensors. The bulk goods flow falls in this case vertically through the observation zone, which is formed by the detector, which has a viewing direction toward the background. A high-pressure nozzle unit downstream from the measuring cell in the falling direction of the bulk goods flow selects flawed parts from the bulk good flow. The fundamental mechanism for detecting flawed parts of this type of sorter is based on the measuring acquisition of the difference in color of the flawed parts in contrast to the components of the remaining bulk goods flow.

An important detail in the design of optical sorting units for transparent objects of this type is, above all, the detection of the optical transparency. In particular with bulk goods, this detection is made difficult by the typically randomized location of the transparent objects in the material flow and the often irregular object geometry.

Even with pure materials, the transmission of the material alone is only an index for the type of material if both object shape and also thickness and attitude are known.

For example, upon the inspection of bulk goods, for example, transparent plastic granules—in transmitted light, strong variations of the transmitted radiation occur already due to the at least relatively undefined attitude and the geometry of the objects. Even upon the inspection of transparent spheres in transmitted light, only a round inspection area is obtained, whose boundaries are a function of the system dimensioning and sphere size. Anomalies may only be detected using a transmitted light configuration in this area. Scratches, foreign particles, and cloudiness of the object surface only result in additional attenuation of the transmitted radiation therein, however. Therefore, corresponding classification is not possible or is hardly possible on the basis of the transmission of bulk goods ascertained in a transmitted light configuration.

U.S. Published Application 2006/0016735 A1 describes a sorter for transparent granules, which fall from a belt conveyor along a trajectory through two detector units situated along the trajectory, of which one records the front side of the granules and the other records the rear side of the granules, each using one camera and one background associated with the camera. By comparing front and rear recordings, the transparency of the components can be concluded and flawed parts can be separated out using a compressed air nozzle on the basis of a criterion. The camera images exclusively acquire light components reflected on the granule surfaces in this configuration, so that an acquisition of flaws enclosed in the granules is not possible.

U.S. Pat. No. 5,442,446 describes a device for examining transparent containers, in particular in regard to their fill level, which provides a light source, whose light passes coaxially in the viewing direction of a detector through a container to be examined, is reflected on a retroreflector situated to the rear of the container, and is acquired by the detector. In addition, two further light sources are provided to the rear of the container, whose emitted light beams penetrate the container in transmission and are also acquired by the detector.

EP 0 379 281 describes a device for examining fabric structures, light from a light source being directed for this purpose via a corresponding deflection mirror onto the surface of a fabric substrate to be examined, under which a retroreflector is provided. The light beams reflected back on themselves are also acquired by a detector unit in this case.

EP 0 372 241 B1 describes an optic configuration for three-dimensional shape acquisition, using which irregularities of a transparent film may be acquired in particular. Light from a light source passes through the film in transmission and is reflected on a retroreflector attached in the beam direction behind the film. The reflected light component is acquired by a video camera for further analysis.

SUMMARY OF THE INVENTION

The device according to the invention determines the transmission of transparent components of a material flow in wide limits independently of the attitude and shape of the objects and to classify the objects, depending on the set testing task and type of object, according to at least one of the following criteria:

transparency,
material or type of material,
geometrical shape anomalies,
defects, such as enclosed air bubbles or scratches or fractures,
embedded foreign bodies, such as absorbed foreign bodies, and
surface defects or contamination on the surface.

Furthermore, a method is to be specified, using a classification which can be implemented in the simplest and most reliable way possible.

According to the invention, a device for the classification of transparent components of a material flow on the basis of their transparency and further object-specific optical properties includes, at least along the optical axis of the optical detector unit, a retroreflector indirectly or directly downstream in the detector viewing direction from the material flow, an illumination unit including at least two light sources, the first light source emitting light of a first type and the second light source emitting light of a second type, the light of at least the first light source being incident on the material flow longitudinally relative to the optical axis, and the optical detector unit is selectively detecting the light of both light sources. In a first alternative variant of the invention, the light of the second light source illuminates the material flow with an uplighting source, that is, the light being incident on the material flow distributed flatly and not longitudinally relative to the optical axis of the detector unit. In a second alternative variant of the invention, in contrast, the light of the second light source is incident on the material flow longitudinally relative to the optical axis.

In a first advantageous embodiment, the components of the material flow are guided as closely as possible over a flat retroreflector, for example, like a retroreflective film or an array of glass beads or microprisms, the viewing direction of the optical detector unit, which is preferably implemented as a camera, being directed toward a component in the material flow and the reflector located behind it. An illumination beam path, which is coincident with the optical axis of the camera unit, is reflected in the beam path of the camera in the direction toward the component of the material flow. In this way, recordings of level transparent components, for example, on glass panes, may be obtained using the camera unit, which correspond to the recordings using a so-called transmitted light configuration. Because the light beams penetrate the particular transparent components two times, due to the retroreflector, changes of the transmission of the components to be examined may be observed with correspondingly higher contrast using the camera unit.

For components which do not have level surfaces, all beam paths which are incident on the retroreflector are additionally reflected back to themselves practically without offset and also reach the camera again. In the example noted above of spherical objects, nearly complete lighting of the spheres can be caused using this configuration. In the images of sufficiently transparent spheres, practically only the outer edges of the spheres are still visible. Corresponding advantages are also obtained for all transparent objects having different shapes.

Through the additional uplighting illumination of the components according to the invention, differences between scattering particles and absorbing particles, for example, foreign particles in the components may be made visible. In combination with the results from the analysis of the retroreflective beam path, a further classification of the observed anomalies is thus possible. If the components in the material flow have light from at least two different ranges of the electromagnetic spectrum transmitted through them according to the second specified alternative embodiment, that is, light of a first light source and a second light source is reflected in each case longitudinally relative to the optical axis of the optical detector unit, the material or the type of material can be ascertained from the comparison of the transmissions in the different spectral ranges. The different ranges of the electromagnetic spectrum are the UVA, the UVB, the UVC, the x-ray, or the gamma ray range, the visible range of the spectrum (VIS), the near infrared (NIR), middle infrared (MIR), or far infrared (FIR) range, or the range of terahertz waves.

One example of a combination of two different ranges is a combination of the UVC and the visible spectral ranges. Using such a combination, it is possible, for example—based on a comparison of the transmissions in the visible and in the UVC ranges—to differentiate diamonds from quartz. This can be performed using a very simple method, in that the quotient of the transmission in the UVC and in the visible ranges of the spectrum is calculated for each component and the relative transmissions thus obtained are compared to a fixed threshold or target value.

A method for classifying components within a material flow which is based on the use of the present device is explained hereafter.

Components contained inside a material flow are optically acquired with the aid of a detector unit, whereby detector data results, in the form of image data, which is to be subjected to an image data analysis. As a function of the particular components to be classified, a texture module which theoretically describes the particular component to be classified is created, which is capable of describing the particular components within the material flow according to shape, size, and their optical properties at least in coarse approximation. The texture module contains parameters to be specified in greater detail, however, whose definition forms a virtual reference pattern, a so-called elementary pattern.

To define the texture model parameters, the detector data, that is, the image data which the detector unit generates from a material flow to be classified, are subjected to a feature extraction, on the basis of which the parameters which define the texture module in greater detail may be defined. In the scope of the feature extraction, the detector or image data are studied according to patterns predetermined by the texture model and/or visually perceptible special features, through whose analysis and/or corresponding scaling, concrete parameters which define the texture model in greater detail may be derived. In addition, parameters applicable for all image data may be derived from the feature extraction, the so-called global parameters, such as the spatial observation angle, at which the detector unit acquires the material flow, or the illumination conditions, etc.

After the definition of the parameters which describe the components in greater detail and also the global parameters applicable for all components within the material flow, the parameterized texture module having a texture to be expected results, resulting in both the size and shape of every individual pattern derivable from an elementary pattern and its optical properties are known. Furthermore, the position of all individual patterns within the material flow can be defined on the foundation of a configuration scheme derived from the parameterized texture module.

Deviations, in the meaning of possible defects, may be recognized by comparison of the individual patterns, which can be selected and localized with the aid of the parameterized texture module from the image data of the detector unit, to the elementary pattern, which is also derivable from the texture module and is used as a reference pattern.

A corresponding class assignment is performed for each position of an individual pattern located within the image data set on the basis of a position-dependent classification. That is detected individual patterns, which are in the central area of the image obtained by the detector unit, are subject to many fewer interfering influences, caused by shadows, image edge distortions, etc. Then the individual patterns which lie in the image edge area, so that stricter classification criteria applies for the individual patterns detected in the image central area than for those in the image edge area.

In addition, it is possible to subject deviations from a pre-determined elementary pattern, even within an individual pattern, to a position-dependent classification, in order to thus extensively consider system-related detection irregularities. For example, detection irregularities which are a function of the illumination and viewing conditions at the location of an elementary pattern to be inspected. Shape-related shadow effects on a component may be considered in this way.

In addition, flaws detected in the elementary pattern, if in areas of the elementary pattern which are noncritical for later use of the detected component, may be accepted. If the components to be checked relate to optical lenses, for example, which are delivered as the final product in a frame, flaws near the edge within the particular lens, which are covered by the frame in any case, may be accepted.

Finally, an actuator in connection with the classification allows a separation of the components classified as discard or flawed parts from the material flow.

The method described above is based on the pre-definition of a texture module, in which the shape and the material and, connected thereto, the optical properties of a component to be classified within the material flow are considered in the following way. A virtual pure model of the particular component is generated on the foundation of a known object shape and known optical properties of a component to be classified. The pure model is then transferred into an object model, which is used as the foundation for the inspection tasks or classification to be observed. If present, process anomalies which influence the pure model and which can be described in the scope of an anomaly model are incorporated in the object model. Otherwise, a sufficiently precise knowledge of the fraction to be selected or marked from the material flow is often sufficient.

In further consideration of known parameters, which describe the optical inspection system, that is, the illumination and image recording properties of the detector unit, a scene model follows from the object model, on whose foundation a texture model, which can be parameterized, can finally be defined by prediction of the image data recorded using the detector unit.

The texture model is composed of at least one elementary pattern and a configuration scheme, according to which the elementary pattern can be situated in position and attitude. The elementary pattern corresponds to the ideal individual pattern of a component to be classified. Fundamentally, the elementary pattern and the configuration scheme may have stochastic variations. The following cases may be differentiated depending on the strength of the variations:
1. Structural structure type, that is, no type of stochastic variation occurs.
2. Structural-statistic structure type, that is, stochastic variations occur, but elementary patterns may be recognized.
3. Statistical texture type, that is, stochastic variations occur to an extent at which the elementary pattern may no longer be recognized.

BRIEF DESCRIPTION OF THE DRAWINGS

The invention is explained for exemplary purposes hereafter without restriction of the invention on the basis of exemplary embodiments with reference to the drawings. In the figures.

DESCRIPTION OF THE INVENTION

Figure 1:
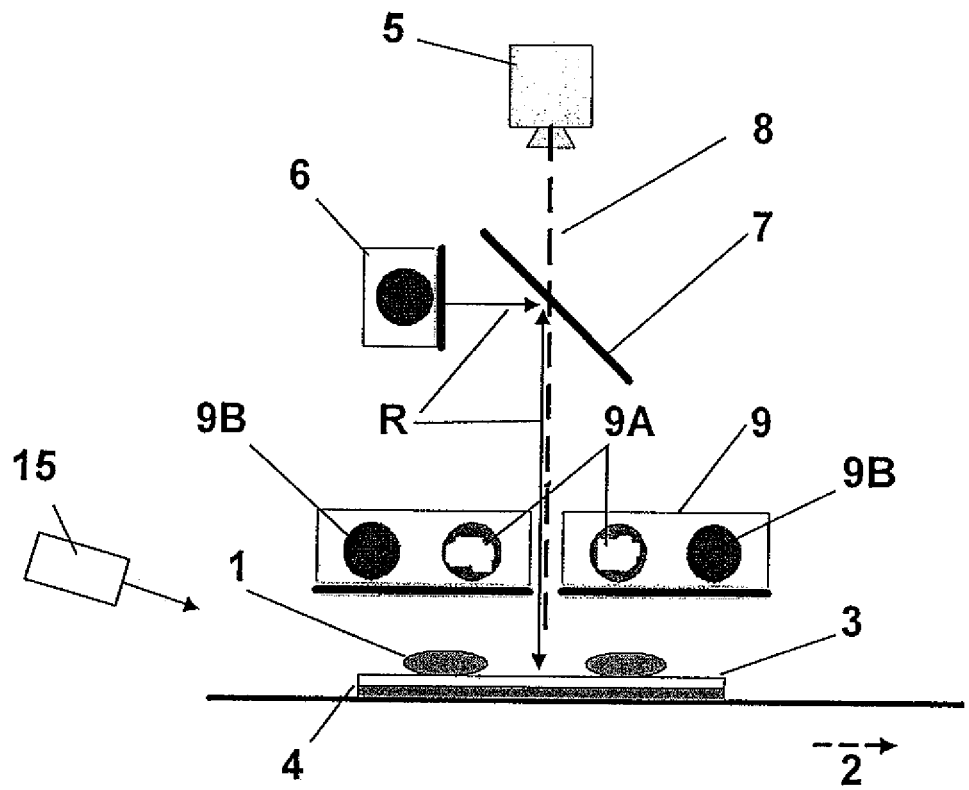
FIG. 1 shows a schematic illustration of a device for the optical recognition of foreign particles in (partially) transparent components of a material flow.

FIG. 1 shows the schematic construction of a device in accordance with the invention for the recognition of foreign particles in (partially) transparent components 1 of a material flow. In the example shown, the components 1 are lenticular objects, which are produced in an extruder and are conveyed below the device along the conveyance direction 2. A satin-finished glass pane 3 is located below the objects 1, which, on the one hand, prevents contact of the objects 1 with the retroreflective film 4 and, on the other hand, has the result that the radiation detected using the camera 5 is not modulated by the fine structure of the reflector 4. The illumination 6 using a first light source emits light for the retroreflective beam path R, which is reflected via a half-silvered mirror 7 along the optical axis 8 of the camera 5.

The objects 1 are additionally illuminated using an uplighting illumination 9, which provides two types of light sources, a second and a third light source 9A and 9B, which each emit in different spectral ranges and additionally illuminate the objects 1 or the retroreflector 4 from different angles.

In the example shown, the camera 5 is implemented as an RGB color line camera, the illumination 6 emits red light, the light 9A emits green light, and the light 9B emits blue light. An analysis is performed according to a method described hereafter.

Fundamentally, the device described above, uses a simultaneous inspection of at least partially transparent components in transmitted light observation and also in uplighting observation which makes use of the following findings:

Geometric anomalies stand out in the uplighting observation as light areas and appear dark in the transmitted light observation, in contrast, substance anomalies, such as embedded foreign particles, stand out as dark areas in both uplighting and also transmitted light observation. Through a corresponding linkage of recordings in uplighting and transmitted light modes, one can thus differentiate between foreign particles and geometric flaws. In addition, the illuminating beams are always in the viewing range of the camera due to the retroreflector beam path being independent of the object geometry. That is, the components are lighted uniformly in broad limits independently of their shape. The transparent components, even have light transmitted through them twice, so that transmission changes are shown as being squared.

By optionally providing a further illumination unit 15, which is situated laterally above the material flow to be detected and emits light which differs through at least one physical property, for example, wavelength, polarization, amplitude, frequency, and/or pulse modulation, etc., from the light which is emitted from the first three light sources 6, 9A, 9B above, superficially deposited contaminants, for example, in the form of dust, may be recognized on the individual objects 1, which may be classified as permissible contaminants for the purposes of classification.

A higher signal value results in the camera 5 in the event of scattering surfaces through lateral illumination, preferably situated below a flat angle of incidence. Because the surface of the objects 1 fundamentally hardly results in scattering, high camera signal values only result in the event of superficial contaminants or anomalies.

Through corresponding segmenting of the camera signals from this inspection channel (referred to as "dust channel" hereafter), that is, through suitable selective detection of the light components originating from the additional illumination unit 15, dust segments may be obtained. Therefore, only positions for which a segment exists in the uplighting channel and in the retroreflective beam channel and no segment exists in the "dust channel" are thus to be classified as absorbing foreign particles. If the total size of all segments having this property exceeds a permissible threshold for an object, an ejection of the particular object results.

Figure 2:
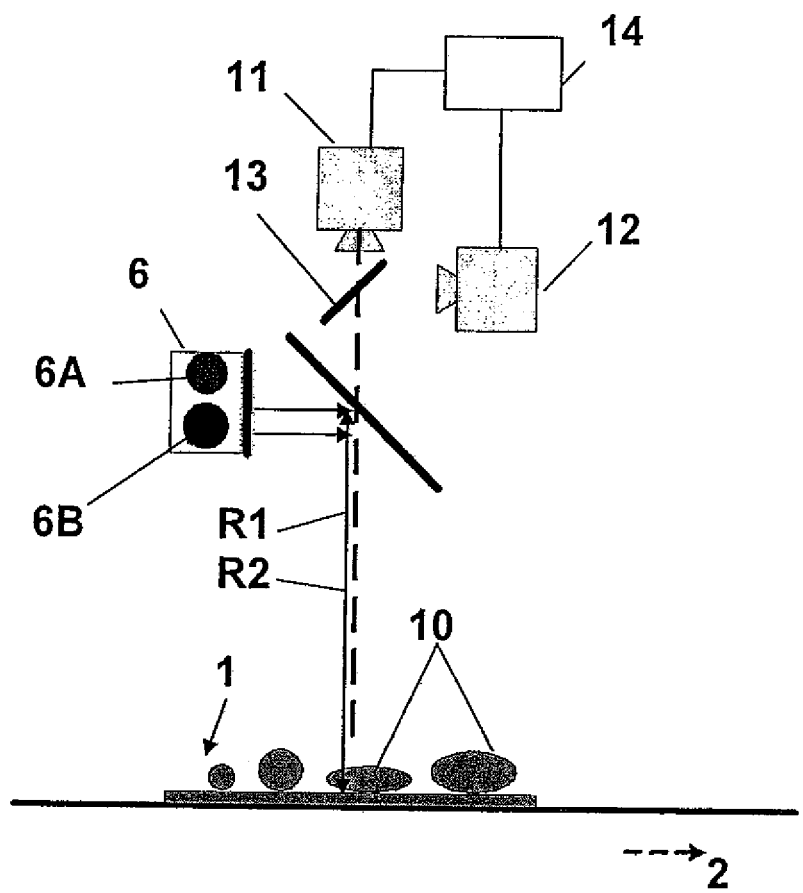
FIG. 2 shows a schematic illustration of a device for the optical recognition of the material type of (partially) transparent components of a material flow.

FIG. 2 shows an embodiment of the device according to the invention which is capable of recognizing the material type of transparent objects 1. The recognition of diamonds in a goods flow 10, which contains quartz and diamonds as partially-transparent components, is cited as a concrete differentiation example. In this configuration, the illumination unit 6 has two light sources 6A and 6B, whose light beams R1, R2 are coupled via a half-silvered mirror 7 along the optical axis 8 of the camera 11 as the retroreflective beam path. It is assumed that the first light source 6A is a white light fluorescent tube for the visible spectral range and the other light source 6B is a UVC fluorescent tube.

A VIS matrix camera 11 is used as the camera 11. Furthermore, a UVC matrix camera 12 is provided, which detects the transmitted UVC light reflected via a wavelength-selective beam splitter 13. The material properties, that is, the substance of the examined objects 1, are concluded from the detected differences of the transmission of the objects in the two spectral ranges using a classifier 14, to which the signals of both cameras 11 and 12 are applied.

The mode of operation of the device according to the invention on the foundation of the analysis method according to the invention is explained in greater detail hereafter on the basis of four examples:

1. Recognition of Foreign Particles in Transparent Solids

In this application, absorbing foreign particles in transparent solids are to be recognized, for example, contaminants in glass products. Air bubbles and deviations on the object surface and also object deformations may be viewed as permissible in this case and therefore cannot be recognized as flaws.

The transparent solid is composed, for example, of multiple ellipsoids which are connected to one another. The ellipsoids are additionally cross-linked in a geometric structure. The edge of the ellipsoids has a reduced transmission, because of which a dark edge results on the detector image in the retroreflective beam channel. The image through the camera of an ideal ellipsoid thus corresponds to a so-called elementary pattern. Because processing anomalies which result in object deformations develop over a longer period of time, a so-called structural texture type can be used as the basis for every analysis range of the detector data.

The parameters of the texture module may be defined on the basis of the detector data features using a global approach. Parameters are, for example, the length of the half-axes of the elementary pattern and the parameters of the geometric structure of the configuration scheme as well as the brightness of the elementary pattern. The individual patterns can be localized on the basis of the patterns of the configuration scheme. In contrast to air bubbles and deviations on the object surface, absorbing particles are imaged as dark objects in both the uplighting channel and also in the retroreflective beam channel of the detector and may be recognized as deviations. The position-dependent classification evaluates the deviations within the ellipsoids in order to compensate for transmission changes caused by position-dependent solid thickness.

2. Recognition of Air Bubbles in Gel Spheres

While air bubbles are unimportant in transparent solids such as spherical plastic granules, they are a clear indication of a defect of the gel spheres in the production of gel spheres having embedded liquids and powders, which must therefore be ejected from the flow of produced articles. In addition, the smoothness of the surface of the gel spheres is to be defined and the roundness and the diameter are optionally also to be analyzed for aesthetic reasons. Foreign particles cannot occur because of processing and are therefore not to be analyzed.

The gel spheres are firstly guided over a shaker. Randomly situated images of the gel spheres result on the detector. The image of an ideal gel sphere corresponds to the elementary pattern. The gel spheres vary in roundness, transparency, diameter, etc. A stochastic configuration scheme and an elementary pattern having stochastic variations, which is designated as the structural-statistic texture type, results.

The variations of the gel spheres are imaged on parameters of the elementary pattern. Parameters result for diameter, brightness, roundness, etc., of each elementary pattern. Because hardly any correlation exists between the positions of the individual elementary patterns, the global parameter definition is not used and the elementary patterns are localized directly. The edge of the gel spheres has a reduced transmission, because of which a dark edge results in the retroreflective beam channel of the detector. It is possible that no changes are recognizable in the uplighting. The elementary pattern thus corresponds to a dark ring in the retroreflective beam channel with no change existing in the uplighting under certain circumstances.

Because the variation of each gel sphere is to be analyzed and the gel spheres are randomly situated, there are no analyzable global parameters of the texture model and the individual patterns are to be localized directly on the basis of the features of the detector data.

The individual patterns may be detected by segmenting with subsequent blob analysis. The deviation detection recognizes deviations within the individual patterns, which are classified thereafter.

The images of air bubbles also have a dark edge in the retroreflective beam channel, whereby a deviation is detectable. The position-dependent classification is necessary in order to recognize the images of air bubbles in the edge of the individual patterns. The smoothness is optionally additionally analyzed on the basis of the uplighting channel.

3. Recognition of Diamonds in Rock Containing Quartz

In this application, diamonds are to be recognized. Unpredictably varying rock thicknesses and surface roughnesses result due to the deviations of the natural starting material. The rock attitude and the rock shape vary strongly, but because the detector image of an ideal diamond can be defined as an elementary pattern, a structural-statistic texture results in spite of the strongly varying rock attitude and rock shape. The material selection for diamond recognition is implemented on the basis of the transmission behavior in the visible and UVC ranges. The transmission values are ascertained using retroreflective beam paths in the visible and UVC ranges. The transmission behavior in the visible and UVC ranges is not only influenced by the material properties, but also by the unpredictable rock shape and rock roughness. Because these transmission changes due to rock shape and rock roughness act as identical factors on the visible and UVC ranges, these effects may be eliminated by pixel-based division of the transmission in the UVC range from transmission in the visible spectral range. A relative transmission image results as a feature from the detector data. The individual patterns may be localized on the basis of the relative transmission imaging via a segmenting of regions having similar values. Because no defects are to be recognized, deviation detection is not necessary and a material-selective classification can be performed directly on the basis of the average transmission of the individual patterns, in order to recognize diamonds.

4. Recognition of Embedded Particles in Lenticular Glass Blanks

Similarly, but in contrast to the "recognition of foreign particles in transparent solids" described under example 1, in this application absorbing foreign particles are to be recognized. Air bubbles and object deformations are also permissible and therefore cannot not be recognized as flaws. In addition, in this application the flaw tolerances are sufficiently small that even ultrasmall dust particles on the object would already result in ejection. Therefore, in this application a differentiation between embedded particles and superficial particles is necessary, with only objects having embedded particles being ejected.

The glass blanks are guided past the inspection system in the travel direction as an object chain. An individual glass blank corresponds to the elementary pattern described above. A structural texture type results through the object chain, that is, no stochastic variations occur. The individual glass blanks may be segmented and superimposed with the elementary pattern and transmission changes which are caused by the position-dependent solid thickness may be compensated for on the basis of the edge of the glass blanks.

Absorbing particles are imaged, in contrast to air bubbles and deviations on the object surface, as dark objects in the uplighting channel and in the retroreflective beam channel of the detector and may be recognized as deviations. Coherent segments having deviations may be obtained by segmenting of the uplighting channel and retroreflective beam channel. If the positions of the segments in the uplighting channel and retroreflective beam channel overlap, an absorbing particle exists. The particle can also be a permissible contaminant (dust) on the surface, however. Therefore, a further analysis channel is required. A higher value results on the detector through lateral illumination at a flat angle of incidence in the event of scattering surfaces or scattering particles on the surface. Because the surface hardly results in scattering, high detector values only result due to permissible superficial contaminants. Dust segments may be obtained by segmenting this "dust channel". Only positions for which a segment exists in the uplighting channel and in the retroreflective channel and no segment exists in the "dust channel" are thus to be classified as absorbing foreign particles and result in ejection of the object if the total size of all segments having this property for an object exceeds a permissible threshold.

LIST OF REFERENCE NUMERALS 1 flow of (partially) transparent goods
2 conveyance direction
3 satin-finished glass pane
4 retroreflective film
5 camera unit
6 illumination for the retroreflective beam path
7 partially-transparent mirror
8 optical axis of the camera
9 uplighting illumination
9A, 9B different ranges of the uplighting illumination
6A white light fluorescent tube for the visible spectral range
6B UVC fluorescent tube
11 matrix camera for the visible spectral range (VIS)
12 UVC sensitive matrix camera
13 wavelength-selective beam splitter
14 classifier
15 illumination unit

The invention claimed is:

1. A device for classification of a transparent component of a moving material flow comprising:
    an optical detector unit with an allocatable optical axis directed toward the moving material flow;
    at least one illumination unit for illuminating the material flow from a space spanning over the moving material flow also containing the optical detector unit;
    a classifier, for classifying the component based on information which is recorded from the component using the optical detector unit and at least one decision criterion for providing the classification of the moving material flow;
    a retroreflector located in a detector viewing direction behind the moving material flow at least along the optical axis of the detector unit; and wherein
    the illumination unit includes at least two light sources which each illuminate the material flow with different light beams, with a first light source emitting light of a first type and a second light source emitting light of a second type;
    the light of at least the first light source is incident on the moving material flow longitudinally relative to the optical axis;
    the optical detector unit selectively detects the light of both light sources; and
    the light of the second light source illuminates the moving material flow with incident light wherein the light of the second source is incident to illuminate an area of the moving material flow and is not incident longitudinally relative to the optical axis of the detector unit.

2. A device for classification of a transparent component of a moving material flow comprising:
    an optical detector unit with an allocatable optical axis directed toward the moving material flow;
    at least one illumination unit for illuminating the moving material flow from a space spanning over the moving material flow also containing the optical detector unit;
    a classifier, for classifying the component based on information which is recorded from the component using the optical detector unit; and
    at least one decision criterion used for providing the classification of the moving material flow;
    a retroreflector located at least along the optical axis of the detector unit, behind the moving material flow in a detector viewing direction; and wherein
    the illumination unit comprises at least two light sources which each illuminate the moving material flow with different light beams, with a first light source emitting light of a first type and a second light source emitting light of a second type;
    the light of at least the first light source is incident on the moving material flow longitudinally relative to the optical axis;
    the optical detector unit selectively detects light from both light sources; and
    the light of the second light source is incident onto the moving material flow longitudinally relative to the optical axis.

3. The device according to claim 1, comprising:
    at least one third light source which illuminates the moving material flow as an incident light source and the light of the at least one third light source is a third type which the optical detector unit is capable of selectively detecting.

4. The device according to claim 2, comprising:
    at least one third light source which illuminates the moving material flow as an incident light source, and the light of the at least one third light source is a third type which the optical detector unit is capable of selectively detecting.

5. The device according to claim 1, comprising:
a reflective device located along the optical axis of the detector unit for reflecting at least the light of the first light source parallel relative to the optical axis of the detector unit.

6. The device according to claim 2, comprising:
a reflective device located along the optical axis of the detector unit for reflecting at least the light of the first light source parallel relative to the optical axis of the detector unit.

7. The device according to claim 5, wherein:
the reflective device is a half-silvered mirror.

8. The device according to claim 1, wherein:
the light of the at least first and second light sources differs in at least one of the following properties: wavelength, polarization or modulation.

9. The device according to claim 2, wherein:
the light of the at least first and second light sources differs in at least one of the following properties: wavelength, polarization or modulation.

10. The device according to claim 3, wherein:
the light of the third light source differs in at least one of the following properties from the light of the first and second light sources: wavelength, polarization or modulation.

11. The device according to claim 1, wherein:
spacing between the moving material flow and the retroreflector is less than 10% of the spacing between the optical detector unit and the moving material flow.

12. The device according to claim 2, wherein:
spacing between the moving material flow and the retroreflector is less than 10% of the spacing between the optical detector unit and the moving material flow.

13. The device according to claim 1, wherein:
the retroreflector has a two-dimensional area which is greater than an area of the moving material flow which can be acquired by the optical detector unit and is oriented essentially parallel to the plane of propagation of the moving material flow.

14. The device according to claim 2, wherein:
the retroreflector has a two-dimensional area which is greater than an area of the moving material flow which can be acquired by the optical detector unit and is oriented essentially parallel to the plane of propagation of the moving material flow.

15. The device according to claim 2, wherein:
light of the first and second light sources is directed longitudinally relative to the optical axis, differs in wavelengths originating from at least two different spectral ranges of the electromagnetic spectrum, the spectral ranges being UVC, UVB, UVA, VIS, NIR, MIR, FIR, or terahertz ranges of visible light, and the light sources emit a continuous spectrum or a line spectrum in the ranges.

16. The device according to claim 3, wherein:
the second and third light sources illuminate the moving material flow as incident illumination from different angles and light which is incident on the moving material flow from the different angles differs in one of the following properties: wavelength, spectral composition, polarization or modulation.

17. The device according to claim 1, wherein:
the optical detector unit includes spectrally sensitive receiving channels each having different sensitivity for different spectral ranges.

18. The device according to claim 2, wherein:
the optical detector unit includes multiple spectrally sensitive receiving channels each having different sensitivity for different spectral ranges.

19. The device according to claim 17, wherein:
the receiving channels are sensitive to different polarization states of the light returned from the moving material flow.

20. The device according to claim 1, comprising:
a material layer situated between the retroreflector and the moving material flow which is transparent to light in a first spectral range emitted by the first light source and emits light in the first spectral range upon illumination by light of another spectral range emitted by the second light source or another light source.

21. The device according to claim 2, comprising:
a material layer situated between the retroreflector and the moving material flow which is transparent to light of a first of the spectral range emitted by the first light source and emits light in the first spectral range upon illumination by light of another spectral range emitted by the second light source or another light source.

22. The device according to claim 20, wherein:
the material layer is a transparent fluorescent layer.

23. The device according to claim 1, comprising:
a material layer, which changes a polarization state of radiation transmitted between the retroreflector and the moving material flow.

24. The device according to claim 2, comprising:
a material layer, which changes a polarization state of radiation transmitted between the retroreflector and the moving material flow.

25. The device according to claim 3, wherein:
the third light source illuminates the moving material flow at a flat angle of incidence.

26. The device according to claim 4, wherein:
the third light source illuminates the moving material flow at a flat angle of incidence.

27. The device according to claim 21, wherein:
the material layer is a transparent fluorescent layer.

28. The device according to claim 1 wherein:
the at least one decision criterion comprises at least one transparency, material, type of material, geometrical shape anomalies, defects, embedded foreign bodies, surface defects or contamination on the surface of the moving material flow.

29. The device according to claim 28 wherein:
the defects include at least one of air bubbles, scratches or fractures of the moving material flow and the embedded foreign bodies include absorbed bodies.

30. The device according to claim 2 wherein:
the at least one decision criterion comprises at least one transparency, material, type of material, geometrical shape anomalies, defects, embedded foreign bodies, surface defects or contamination on the surface of the moving material flow.

31. The device according to claim 30 wherein:
the defects include at least one of air bubbles, scratches or fractures of the moving material flow and the embedded foreign bodies include absorbed bodies.

* * * * *